US00PP20037P3

(12) United States Plant Patent
Giesen

(10) Patent No.: US PP20,037 P3
(45) Date of Patent: May 26, 2009

(54) *ARGYRANTHEMUM* PLANT NAMED 'SAS PINKA'

(50) Latin Name: *Argyranthemum frutescens*
Varietal Denomination: Sas Pinka

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 40 days.

(21) Appl. No.: 11/890,347

(22) Filed: Aug. 6, 2007

(65) Prior Publication Data

US 2009/0044304 P1 Feb. 12, 2009

(51) Int. Cl.
*A01H 5/00* (2006.01)

(52) U.S. Cl. ..... Plt./406

(58) Field of Classification Search ..... Plt./406
See application file for complete search history.

(56) References Cited

PUBLICATIONS

GTITM UPOVROM citation for 'Sas Pinka'as per CA PBR 06–5366; filed Mar. 21, 2006.*

* cited by examiner

*Primary Examiner*—Kent L Bell
(74) *Attorney, Agent, or Firm*—Jondle & Associates, P.C.

(57) ABSTRACT

A new *Argyranthemum* plant particularly distinguished by its large pink inflorescences, a semi-compact and full plant habit, light green foliage and good vigor is disclosed.

1 Drawing Sheet

Genus and species: *Argyranthemum frutescens.*
Variety denomination: 'Sas Pinka'.

BACKGROUND OF THE NEW PLANT

The present invention comprises a new and distinct cultivar of *Argyranthemum*, botanically known as *Argyranthemum frutescens,* and hereinafter referred to by the cultivar name 'Sas Pinka'. The new cultivar originated from a hybridization made in August 2003 in Andijk, The Netherlands. The female parent was the light-pink flowered *Argyranthemum* proprietary line 'AR03-159-1' (unpatented), and the male parent was the pink flowered *Argyranthemum* proprietary line 'AR02-39-1' (unpatented). The seeds produced by the hybridization were sown in January 2004 in Andijk, The Netherlands. A single plant selection was chosen for further evaluation and for asexual propagation in May 2004 in Andijk, The Netherlands.

The new cultivar was created in 2003 in Andijk, The Netherlands and has been asexually reproduced repeatedly by vegetative cuttings and tissue culture in Andijk, The Netherlands and Hillscheid, Germany over a three-year period. The plant has also been trialed at Gilroy, Calif., Andijk, The Netherlands and Hillscheid, Germany. The present invention has been found to retain its distinctive characteristics through successive asexual propagations.

SUMMARY OF THE INVENTION

The following are the most outstanding and distinguishing characteristics of this new cultivar when grown under normal horticultural practices in Gilroy, Calif.

1. Large, pink inflorescences;
2. A semi-compact and full plant habit;
3. Light green foliage; and
4. Good plant vigor.

DESCRIPTION OF THE PHOTOGRAPHS

This new *Argranthemum* plant is illustrated by the accompanying photographs which show overall plant habit including blooms, buds, and foliage of the plant; the colors shown are as true as can be reasonably obtained by conventional photographic procedures.

Figure 1:
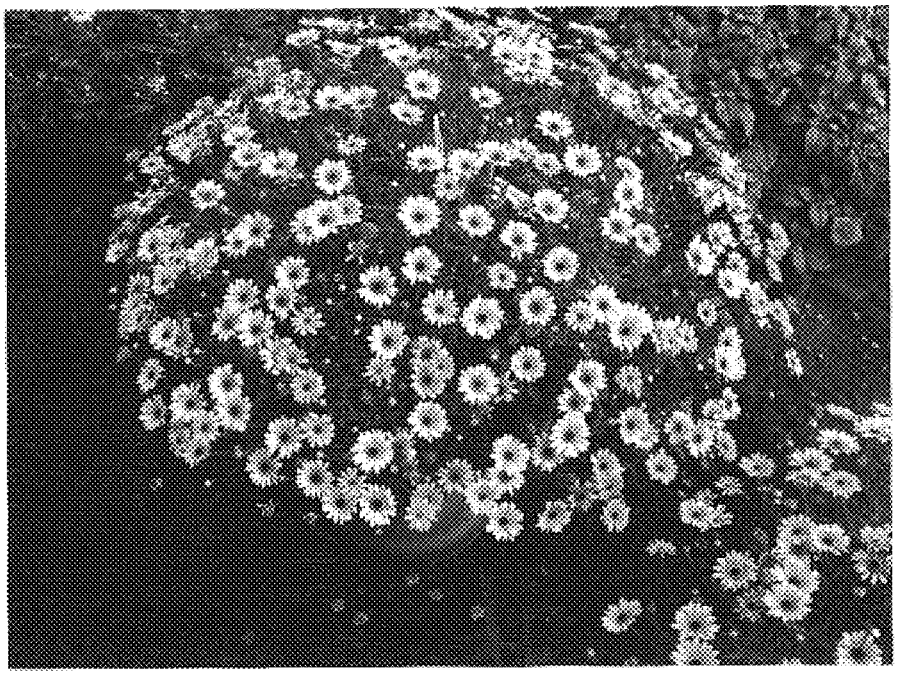

FIG. 1 Overall plant habit including blooms, buds, and foliage of the plant grown outside in a 10-inch basket in the summer in Andijk, The Netherlands in August.

Figure 2:
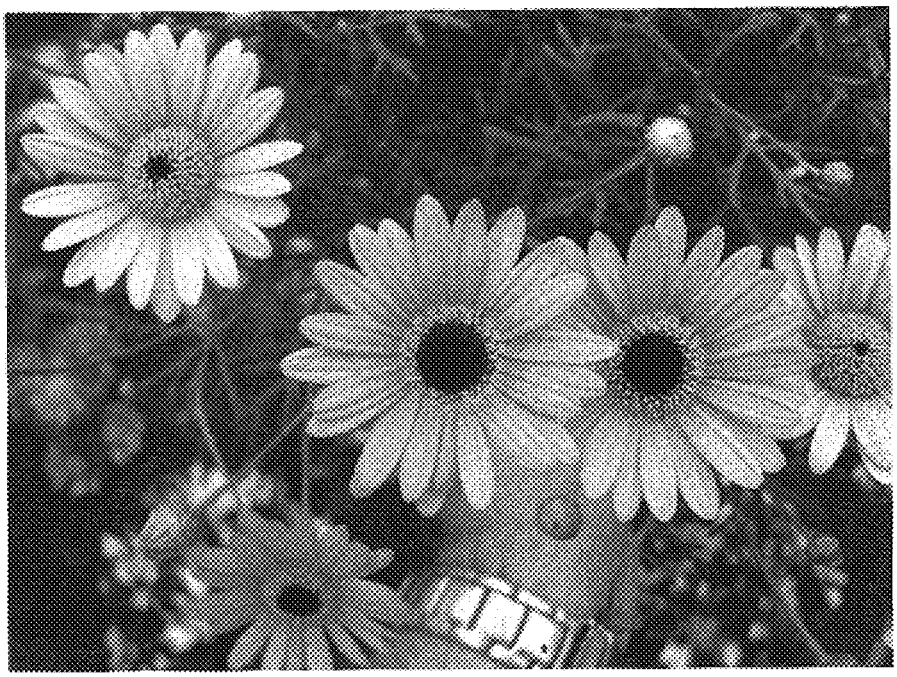

FIG. 2 Close-up of a 3 to 4 month old plant grown in a 5-inch pot in a greenhouse in Andijk, The Netherlands in May.

DESCRIPTION OF THE NEW CULTIVAR

The following detailed descriptions set forth the distinctive characteristics of 'Sas Pinka'. The data which define these characteristics were collected from asexual reproductions carried out in Hillscheid, Germany. The plant history was taken on 16-week-old plants grown in 12-inch pots in the spring in a greenhouse. Two terminal pinches and one plant growth regulator treatment was made at a young plant stage. Color readings were taken in the greenhouse in May under natural light. Color references are primarily to the R.H.S., Colour Chart of The Royal Horticultural Society of London (R.H.S.) (2001 edition). Texture description details were observed under a dissecting microscope.

DESCRIPTION OF THE NEW PLANT

Classification:
*Family.*—Asteraceae.
*Botanical name.*—*Argyranthemum frutescens.*
Parentage:
*Female parent.*—'AR03-159-1' light-pink flowered *Argyranthemum* proprietary line (unpatented).

*Male parent.*—'AR02-39-1' pink flowered *Argyranthemum* proprietary line (unpatented).

Growth:

*Form.*—Upright.

*Habit.*—Semi-compact.

*Growth and branching habit.*—Good, vigorous and freely branching habit.

*Height* (*from top of soil*).—25.0 cm to 30.0 cm.

*Width* (*including inflorescences*).—47.0 cm to 55.0 cm.

*Time to produce a finished flowering plant.*—7 to 9 weeks for a 6-inch pot.

*Outdoor plant performance.*—Used as patio planters, mixed-container plantings, or in garden beds.

*Time to initiate and develop roots.*—14 to 21 days at 68° F. to 74° F.

*Root description.*—Fibrous, freely branching, and white.

Leaves:

*Arrangement.*—Alternate, simple.

*Shape.*—Pinnatifid and deeply divided.

*Apex.*—Acute.

*Base.*—Attenuate.

*Margin.*—Entire.

*Length* (*fully expanded*).—6.0 cm to 7.4 cm.

*Width* (*fully expanded*).—3.8 cm to 6.8 cm.

*Color.*—Immature: Upper surface: RHS 137C to RHS 137D. Lower surface: RHS 143B. Mature: Upper surface: RHS 137A to RHS 137B. Lower surface: RHS 137D to RHS 138A.

*Venation.*—Color: RHS 137C.

*Texture.*—Glabrous.

*Petiole.*—Color: RHS 137B. Length: 0.3 cm to 0.4 cm. Width: 0.2 cm to 0.3 cm. Texture: Glabrous.

Stems:

*Number of branches per plant.*—8 to 12.

*Length.*—19.0 cm to 25.0 cm.

*Diameter.*—0.4 cm to 0.6 cm at the mid-point.

*Internode length.*—1.5 cm to 2.5 cm.

*Color.*—RHS 143D.

*Texture.*—Glabrous.

*Anthocyanin.*—Absent.

Bud:

*Shape.*—Ovate.

*Diameter.*—0.8 cm.

*Length.*—1.0 cm.

*Color* (*just before ray florets unfold*).—RHS N66D.

Inflorescence

*Type.*—Terminal and axillary inflorescences held above foliage; solitary capitulum inflorescence on long peduncles.

*Blooming habit.*—Plants flower continuously from the spring through the fall.

*Quantity of inflorescences per plant.*—20 to 30 with approximately 25 buds.

*Lastingness of individual blooms on the plant.*—11 to 12 days.

*Fragrance.*—None.

*Inflorescence diameter.*—3.9 cm to 4.1 cm.

*Depth.*—0.75 cm.

*Disc diameter.*—1.2 cm to 1.4 cm.

*Disc floret.*—Quantity (per inflorescence): More than 120. Shape: Densely massed, tubular, 5-parted and flared at the apex. Color: Closed: RHS 13A Open: RHS 185A to RHS 60A.

*Tube.*—Color: Immature (closed): RHS 13A near tip and RHS 145A at the middle. Mature: Closest to RHS 145D, but whiter; RHS 46A at apex tips. Length: 0.6 cm. Diameter: 0.1 cm to 0.2 cm. Apex: 5-lobed, acute, somewhat reflexing at maturity. Base: Fused.

*Ray floret.*—Quantity: 23 to 25 arranged in two whorls. Shape and form: Ligulate; the corolla consists of a very short tube or funnel at the base, and the fused ray florets form one long, elliptically shaped ray, horizontally/outwards directed. Length: 1.2 cm to 1.6 cm. Width: 0.45 cm to 0.55 cm. Color: Upper surface: RHS N66D, then RHS 65A and fading at maturity to RHS 75C to RHS 75D; with bases remaining somewhat deeper in color than the middle parts and tips Lower surface: RHS N66C, then RHS 68B and maturing at RHS 69B. Apex: Rounded, or weakly tri-dentate. Base: Fused. Margin: Entire. Texture: Papillose; slight ripple-like lengthwise.

*Peduncle.*—Color: RHS 139D, often with fine lines of anthocyanin coloring of about RHS 181B to RHS 181C. Length: 6.0 cm to 15.0 cm. Diameter: 0.2 cm. Texture: Glabrous.

*Involucral bracts.*—Quantity (per inflorescence): 15 to 17. Shape: Elliptical to ovate. Length: 0.3 cm to 0.4 cm. Width: 0.2 cm to 0.3 cm. Color: RHS 137D and margins are semi-translucent with a papery substance. Apex: Acute. Base: Fused. Margin: Entire. Texture: Glabrous.

Reproductive Organs:

*Androecium.*—Location: Mostly on disc florets only. Quantity: 1 per floret. Filament length: 0.8 cm. Filament color: RHS 11A. Pollen color: RHS 13A. Pollen amount: Moderate.

*Gynoecium.*—Location: Present on ray and disc florets. Quantity per floret: 1. Pistil length: 0.3 cm to 0.4 cm. Stigma: Color: RHS 12A. Style: Color: RHS 145C.

Fruit and seed set: Has not been observed.

Disease and insect resistance: Has not been observed.

COMPARISON WITH PARENTAL AND COMMERCIAL CULTIVARS

'Sas Pinka' differs from the female parent, 'AR03-159-1' (unpatented) in that 'Sas Pinka' has larger, more abundant inflorescences with a more intense flower color than 'AR03-159-1'. Additionally, 'Sas Pinka' has longer branches and internodes than 'AR03-159-1'.

'Sas Pinka' differs from the male parent, 'AR02-39-1' (unpatented) in that 'Sas Pinka' has a larger and more upright plant habit with more abundant stems and leaves than 'AR02-39-1'. Additionally, 'Sas Pinka' has a less intense pink ray floret color than 'AR02-39-1'.

'Sas Pinka' differs from the commercial cultivar 'Pink Wonder' (Patent Status Unknown) in that 'Sas Pinka' has a more compact and fuller plant habit than 'Pink Wonder'. 'Sas Pinka' is earlier to flower with larger inflorescences than 'Pink Wonder'. Additionally, 'Sas Pinka' has lighter green foliage than 'Pink Wonder'.

I claim:

1. A new and distinct cultivar of *Argyranthemum* plant as shown and described herein.

* * * * *